(12) United States Patent
Sarin et al.

(10) Patent No.: US 8,271,066 B2
(45) Date of Patent: Sep. 18, 2012

(54) NON-IMAGING TRACKING TOOLS AND METHOD FOR HIP REPLACEMENT SURGERY

(75) Inventors: Vineet Kumar Sarin, Simi Valley, CA (US); Robert A. Bruce, Ventura, CA (US); William Ralph Pratt, Newbury Park, CA (US); Clyde Ronald Pratt, Somis, CA (US); Roger C. Carignan, Williams, AZ (US)

(73) Assignee: Kinamed, Inc., Camarillo, CA (US)

( * ) Notice: Subject to any disclaimer, the term of this patent is extended or adjusted under 35 U.S.C. 154(b) by 1130 days.

(21) Appl. No.: 12/152,707

(22) Filed: May 15, 2008

(65) Prior Publication Data

US 2008/0221570 A1    Sep. 11, 2008

Related U.S. Application Data

(62) Division of application No. 10/637,304, filed on Aug. 8, 2003, now Pat. No. 8,002,772.

(51) Int. Cl.
*A61B 5/05* (2006.01)

(52) U.S. Cl. ..................................... 600/407

(58) Field of Classification Search .......... 600/407–423; 623/22.11–23.63; 606/130, 102, 1
See application file for complete search history.

(56) References Cited

U.S. PATENT DOCUMENTS

| | | | | |
|---|---|---|---|---|
| 5,086,401 | A * | 2/1992 | Glassman et al. | 700/259 |
| 5,230,338 | A * | 7/1993 | Allen et al. | 600/429 |
| 5,249,581 | A * | 10/1993 | Horbal et al. | 600/407 |
| 5,383,454 | A * | 1/1995 | Bucholz | 600/429 |
| 5,611,353 | A * | 3/1997 | Dance et al. | 600/595 |
| 5,713,906 | A * | 2/1998 | Grothues-Spork et al. | 606/99 |
| 5,772,594 | A * | 6/1998 | Barrick | 600/407 |
| 5,880,976 | A * | 3/1999 | DiGioia, III et al. | 703/7 |
| 5,891,034 | A * | 4/1999 | Bucholz | 600/426 |
| 5,995,738 | A * | 11/1999 | DiGioia et al. | 703/11 |

(Continued)

FOREIGN PATENT DOCUMENTS

CA    2334495 A1    8/2002

(Continued)

OTHER PUBLICATIONS

U.S. Patent Application Publication No. US 2001/0027271 A1; Franck et al.; Oct. 4, 2001.

(Continued)

*Primary Examiner* — Eduardo C Robert
*Assistant Examiner* — Mary Hoffman
(74) *Attorney, Agent, or Firm* — Koppel, Patrick, Heybl & Philpott

(57) ABSTRACT

The invention includes a method of determining a surgical patient's pelvic position and inputting that position into a computer via a tracking system, suitable for use in navigating partial or total hip replacement surgery. The patient is first aligned with anatomical reference points in relation to corresponding locating features on a patient positioner. The positions of index features on the patient positioner are then acquired via a tracking system. Based on the positions of the index features and their known relationship to the locating features, the locations of the anatomical reference features are calculated and a pelvic plane is defined therefrom. The invention also includes a surgical tool for mounting a trackable target to a human bone, suitable for fixation to a human femur. This tool includes a removable bone clamp and a releasable coupling member, integrated with said removable bone clamp.

9 Claims, 5 Drawing Sheets

U.S. PATENT DOCUMENTS

| | | | |
|---|---|---|---|
| 6,002,859 A * | 12/1999 | DiGioia et al. | 703/11 |
| 6,167,292 A * | 12/2000 | Badano et al. | 600/407 |
| 6,187,018 B1 * | 2/2001 | Sanjay-Gopal et al. | 606/130 |
| 6,205,411 B1 * | 3/2001 | DiGioia et al. | 703/11 |
| 6,228,089 B1 * | 5/2001 | Wahrburg | 606/86 R |
| 6,282,437 B1 * | 8/2001 | Franck et al. | 600/429 |
| 6,285,902 B1 * | 9/2001 | Kienzle et al. | 600/427 |
| 6,322,567 B1 * | 11/2001 | Mittelstadt et al. | 606/130 |
| 6,385,475 B1 * | 5/2002 | Cinquin et al. | 600/407 |
| 6,405,072 B1 * | 6/2002 | Cosman | 600/426 |
| 6,430,434 B1 * | 8/2002 | Mittelstadt | 600/426 |
| 6,514,259 B2 * | 2/2003 | Picard et al. | 606/88 |
| 6,546,277 B1 * | 4/2003 | Franck et al. | 600/426 |
| 6,560,354 B1 * | 5/2003 | Maurer et al. | 382/131 |
| 6,662,036 B2 * | 12/2003 | Cosman | 600/411 |
| 6,676,706 B1 * | 1/2004 | Mears et al. | 623/22.4 |
| 6,678,545 B2 * | 1/2004 | Bucholz | 600/426 |
| 6,692,447 B1 * | 2/2004 | Picard | 600/587 |
| 6,697,664 B2 * | 2/2004 | Kienzle, III et al. | 600/427 |
| 6,711,431 B2 * | 3/2004 | Sarin et al. | 600/426 |
| 6,725,080 B2 * | 4/2004 | Melkent et al. | 600/424 |
| 6,856,828 B2 * | 2/2005 | Cossette et al. | 600/429 |
| 6,953,480 B2 * | 10/2005 | Mears et al. | 623/22.11 |
| 8,007,448 B2 * | 8/2011 | Moctezuma de La Barrera | 600/587 |
| 8,010,180 B2 * | 8/2011 | Quaid et al. | 600/424 |
| 2002/0052606 A1 * | 5/2002 | Bonutti | 606/88 |
| 2002/0077540 A1 * | 6/2002 | Kienzle, III | 600/424 |
| 2002/0087101 A1 * | 7/2002 | Barrick et al. | 600/587 |
| 2003/0153829 A1 * | 8/2003 | Sarin et al. | 600/426 |
| 2003/0208122 A1 * | 11/2003 | Melkent et al. | 600/426 |
| 2004/0068179 A1 * | 4/2004 | Jutras et al. | 600/424 |
| 2004/0068260 A1 * | 4/2004 | Cossette et al. | 606/63 |
| 2004/0097952 A1 * | 5/2004 | Sarin et al. | 606/102 |
| 2004/0102792 A1 * | 5/2004 | Sarin et al. | 606/151 |
| 2004/0152955 A1 * | 8/2004 | McGinley et al. | 600/300 |
| 2004/0153062 A1 * | 8/2004 | McGinley et al. | 606/53 |
| 2004/0153080 A1 * | 8/2004 | Dong et al. | 606/80 |
| 2004/0153191 A1 * | 8/2004 | Grimm et al. | 700/114 |
| 2004/0167654 A1 * | 8/2004 | Grimm et al. | 700/114 |
| 2004/0172044 A1 * | 9/2004 | Grimm et al. | 606/130 |
| 2004/0230199 A1 * | 11/2004 | Jansen et al. | 606/91 |
| 2004/0254584 A1 * | 12/2004 | Sarin et al. | 606/102 |
| 2004/0254586 A1 * | 12/2004 | Sarin et al. | 606/130 |
| 2005/0113720 A1 * | 5/2005 | Cinquin et al. | 600/587 |
| 2005/0119561 A1 * | 6/2005 | Kienzle | 600/425 |
| 2005/0203384 A1 * | 9/2005 | Sati et al. | 600/426 |
| 2005/0245820 A1 * | 11/2005 | Sarin | 600/429 |
| 2006/0015030 A1 * | 1/2006 | Poulin et al. | 600/424 |
| 2006/0098851 A1 * | 5/2006 | Shoham et al. | 382/128 |
| 2006/0106292 A1 * | 5/2006 | Anderson | 600/301 |
| 2006/0122495 A1 * | 6/2006 | Kienzle, III | 600/424 |
| 2006/0173293 A1 * | 8/2006 | Marquart et al. | 600/426 |

FOREIGN PATENT DOCUMENTS

| | | |
|---|---|---|
| DE | 10031887 A1 | 1/2002 |
| WO | WO 9915097 | 4/1999 |
| WO | WO 0018306 | 4/2000 |
| WO | WO 0121084 A1 | 3/2001 |
| WO | WO 0164124 A1 | 9/2001 |

OTHER PUBLICATIONS

Supplementary European Search Report Dated Mar. 10, 2009 for Corresponding European Patent Application No. 03749017.4; 6 pp.

Search Report from related European Application No. 09173391.5-1269. Dated: Jan. 11, 2010.

* cited by examiner

NON-IMAGING TRACKING TOOLS AND METHOD FOR HIP REPLACEMENT SURGERY

This application is a divisional of and claims priority of U.S. application Ser. No. 10/637,304 filed on Aug. 8, 2003 now U.S. Pat. No. 8,002,772 in the United States Patent Office.

BACKGROUND OF THE INVENTION

1. Field of the Invention

This invention relates to computer assisted surgery generally and more specifically to computer assisted total hip replacement (THR) or hip arthroplasty operations.

2. Description of the Related Art

Total hip replacement or arthroplasty operations have become increasingly common in the United States, with more than 300,000 such operations occurring annually. Many of the procedures will eventually require revision, due to one of any number of problems. Problems can arise with the implant, which can wear, degrade or even fracture. In other cases, dislocation of the replaced hip can occur, causing extreme pain (not to mention inconvenience and expense). The incidence of dislocation has remained at approximately 2-6 percent, in spite of improvements to technique and materials.

It is known that the incidence of post-surgical dislocation is related to the orientation of the hip replacement components, particularly to the angular orientation of the acetabular shell component in relation to the bony anatomy. See Lewinnek et al., "Dislocation after total hip-replacement Arthroplasties," *Journal of Bone and Joint Surgery*, Vol. 60A, No. 2, PP. 217-220 (1978). The head and neck geometry of the implant is also thought to be a factor.

In spite of the published research, the typical surgeon has not adopted any sophisticated method of navigating hip replacement surgery, in spite of the availability of several techniques. The most prevalent method is to rely on an acetabular impactor tool with a handle placed at an angle predetermined so that if the handle is maintained at a level, horizontal orientation, the acetabular shell will be at a desired angle. This method fails to consider the considerable movement and variation in the patient's pelvic position during surgery; at worst it aligns the shell with the operating table (not necessarily the pelvis). More technological methods have been developed, including the sophisticated method described in U.S. Pat. No. 6,205,411 (and related applications) to DiGioia et al. (2001). The method of DiGioia is an advance over the prior methods (which he summarizes authoritatively in his "Background" section).

DiGioia's method begins with extensive pre-operative imaging, including relatively expensive CT scanning. The pre-operative imagery is then input into a digital computer model, which performs extensive, three-dimensional modeling including range of motion simulations of the patient's anatomy in relation to a specific computer model of a particular implant. Next, in an intra-operative phase, the pre-operative models are registered with intra-operative optical tracking data: a very large number of points are sampled on the pelvis and femur, and the computer fits the data to the pre-operative model. Finally, the implant is positioned to align as closely as possible with the optimized computer model.

The method of DiGioia et al. is complex and requires sophisticated digital and radiological techniques. A need still exists for a simpler method of surgical navigation which will facilitate proper hip geometry with a minimum of pre-operative imagery and expense. It is frequently found that physicians are loath to adopt any methods, and particularly any computerized methods, which are unduly complex, expensive or time consuming. In this they may be forgiven, in light of the increasing economic constraints which burden the modern practice of medicine.

Thus, a need persists for an intra-operative computer assisted hip navigation system which is easily learned, rapidly executed, economically practical, and independent from expensive or exotic pre-operative radiological imagery.

Furthermore, there is a need for specific methods and apparatus which will facilitate tracking a patient's pelvic plane and a patient's femur, in connection with a computer assisted hip navigation system.

SUMMARY OF THE INVENTION

In view of the above problems, the present invention includes a method of determining a surgical patient's pelvic position and inputting that position into a computer via a tracking system, suitable for use in navigating partial or total hip replacement surgery. According to the method, the patient is first aligned with anatomical reference points in relation to corresponding locating features on a patient positioner. The positions of index features on the patient positioner are then acquired via a tracking system. Based on the positions of the index features and their known relationship to the locating features, the locations of the anatomical reference features are calculated and a pelvic plane is defined therefrom.

The invention also includes a surgical tool for mounting a trackable target to a bone, suitable for fixation to a human femur. The tool includes a removable bone clamp and a releasable coupling member, integrated with said removable bone clamp. The coupling member is arranged to mate with a compatible coupling member mounting the trackable target to establish a predetermined spatial relationship between said bone clamp and said trackable target. Furthermore, the coupling member includes a releasable connection between said target and said bone clamp, to remove said trackable target. The connection is capable of re-engaging in a re-engaged position which accurately recaptures said spatial relationship between the bone and said trackable target.

These and other features and advantages of the invention will be apparent to those skilled in the art from the following detailed description of preferred embodiments, taken together with the accompanying drawings, in which:

DETAILED DESCRIPTION OF THE INVENTION

Figure 1:
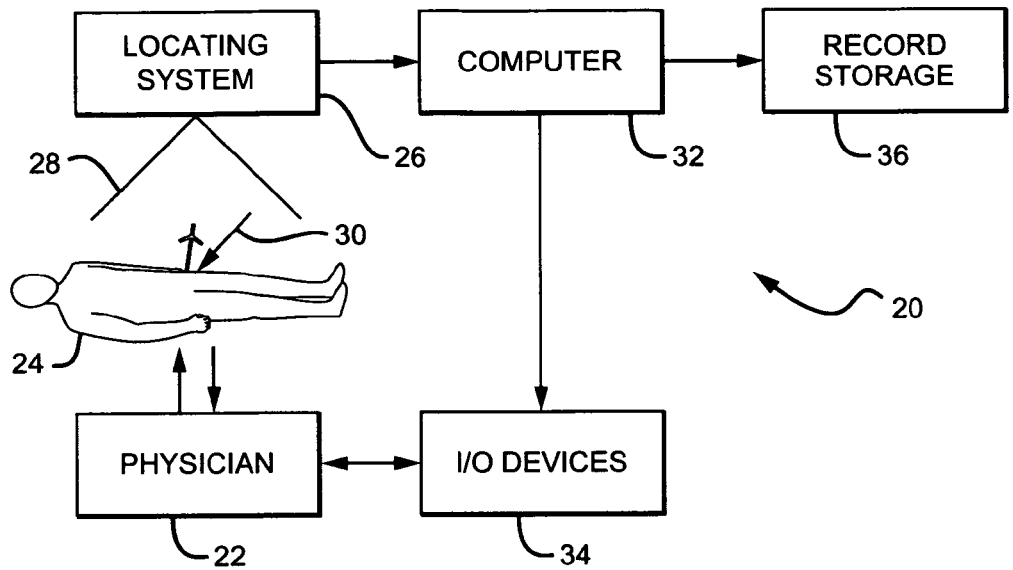
FIG. 1 is a system-level block diagram of the environment in which the invention operates.

FIG. 1 shows a system-level block diagram of a system or apparatus 20 which provides the environment in which the present invention operates. The system or apparatus 20 is generally a computer aided system for navigating orthopedic surgery. A physician or other professional 22 performs a hip surgery (for example, total hip replacement) on a patient 24. An optical or equivalent locator or locating system 26 is disposed near the patient, so that the operating field is encompassed substantially within the field of view 28 of the locator 26. A suitable optical locator is available commercially, for example the "Polaris" available from Northern Digital Inc., in Waterloo, Ontario, Canada. Optical trackers or markers 30 are used during the operation, as more fully described in related application U.S. Ser. No. 10/075,796. The markers 30 allow the locator 26 to acquire the positions and orientations of tools and anatomical reference points, as described below.

The optical locator 26 is interfaced with and outputs tracking data to a digital computer 32, which interprets the optical tracking data as it is received. Using well known geometric relationships, the computer is programmed to deduce from the optical field of view the actual positions and orientations of the markers, and, by extension, the positions and orientations of the instruments and/or anatomical features that are in known relationship to the markers. For example, suitable optical markers utilizing multiple reflective spheres are available from Traxtal Technologies in Toronto, Ontario, Canada. Markers with active light emitting devices such as LEDs are also available and could equivalently be used. Note that typical markers include three or more non-collinear components; this allows the locator and computer to determine not only the positions but the orientation (rotation) of such a marker in space. This capability is exploited in the methods described below.

Figure 2:
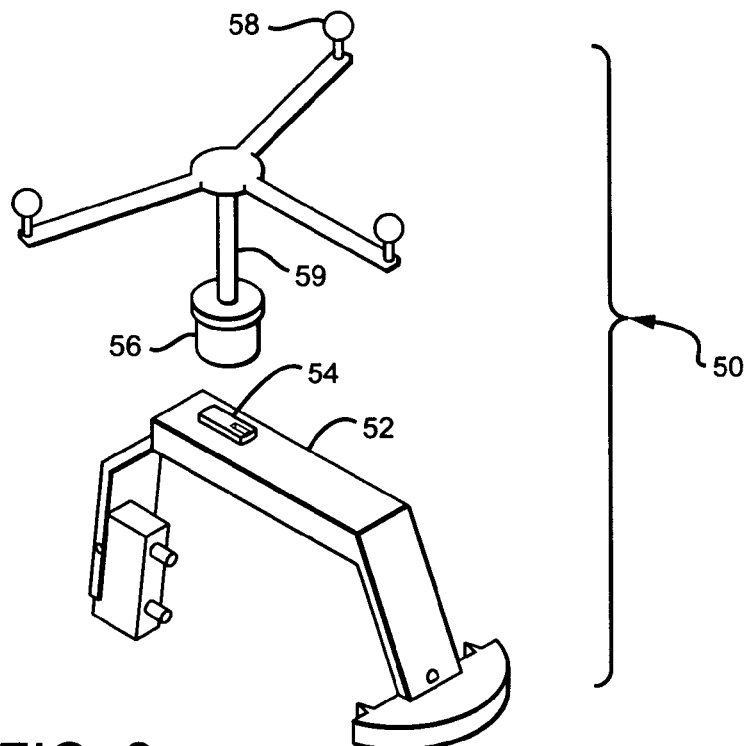
FIG. 2 is an exploded perspective view a trackable femoral marker which attaches to a femur via a clamping device, in accordance with the invention.

Preferably, the computer 32 is also programmed with a user-friendly interface (software) which facilitates the execution of the method of the invention (described below in connection with FIG. 2). The physician or other personnel can view output (for example on a video monitor) and input instructions to the computer 32 via I/O devices 34, which suitably could include a monitor, keyboard, printer, foot pedals, and other input/output devices such as conventional "mouse" or similar pointing devices.

Preferably, the system also includes a record storage device 36 such as a CD-R drive, and/or simply a printer which prints out a summary of the operation and patient data for future reference or medical archiving.

Methods for computer assisted surgical navigation during hip replacement surgeries are described in other patent applications. See, for example, U.S. application Ser. No. 10/075, 796 incorporated herein by reference.

The present invention provides apparatus and method for tracking a femur and a patient's pelvis, suitable for use in connection with any compatible computer assisted hip navigation system. The methods and apparatus described and claimed are useful in the context of the related applications (for example, Ser. No. 10/075,796) but are not limited in their applicability to the exact methods of those applications. The present apparatus and methods are useful in any context in which it is desirable to accurately and conveniently track the position and/or orientation of a patient's femur or pelvis.

The apparatus of the invention is fixable to the femur in a firm and fully engaged position which does not allow slippage or rotation, but without the use of bone screws, pins or any other bone damaging devices. Specifically, in accordance with the invention a trackable marker is attachable to the femur by a device which does not penetrate the outer cortical (hard) shell of the bone. It is permissible, in accordance with the invention, to use aggressively textured surfaces, which could include spikes or cleats which do not fully penetrate the outer cortical shell. Specifically, it is important that the device should not intrude into the upper femoral canal. The inventors have determined that bone screws or pins are not suitable for attaching a marker to the upper femur during hip replacement surgery. Any such penetrating screws or pins would interfere with preparation of the femoral canal and insertion of a trial or permanent hip stem. Furthermore, penetration into the bone would reduce the structural integrity of the bone. The structural integrity of the greater trochanter, for example, should not be compromised; this structure is subjected to high stress due to the biomechanics of the hip joint.

In accordance with a first aspect of the invention, a femoral tracking marker includes a fixing device for affixing a trackable target to a human femur. One embodiment is shown in FIG. 2. The tracking marker (generally at 50) comprises: a removable bone clamp 52; and a releasable coupling 54, integrated with or fixed to the bone clamp 50 and arranged to mate with a compatible coupling 56 on a trackable target 58. Preferably, the trackable target is connected to the coupling 56 by an elongated stem 59, which need not be straight as shown. The coupling of 54 and 56 permits releasable connection between the target 58 and the bone clamp 50 in such a way that a predetermined spatial relationship is established and re-established between the bone clamp and the trackable target 58 whenever the coupling is in mated position, notwithstanding any disconnect/reconnect cycles of the coupling. By extension, provided that the bone clamp remains fixed vis a vis the clamped bone, an initially established spatial relationship between the clamped bone and the trackable target can be re-established, notwithstanding any number of connection and disconnection cycles of the releasable coupling. This allows a surgeon freedom to remove the target for convenience, then reattach the target and resume bone tracking without loss of accuracy.

Figure 3:
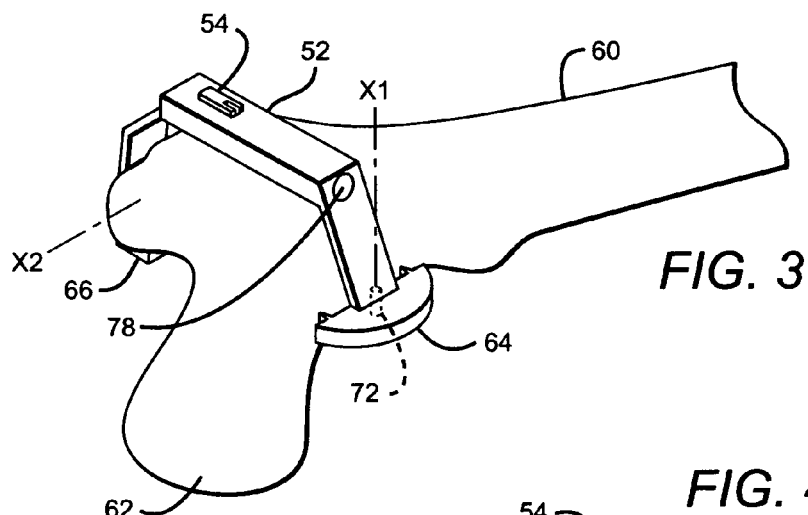
FIG. 3 is a perspective view of the trackable femoral marker of FIG. 2, fixed in a typical position on a human femur.

FIG. 3 shows the bone clamp portion 52 of the femoral tracking marker assembly 50 in operating position: fixed to a femur 60 by clamping about the greater trochanter. This figure shows a suitable manner of mounting the femoral fixing device on a human femur. Specifically, a first jaw 64 is arranged to engage the anterior aspect of the greater trochanter 62; the second jaw 66 is arranged opposite, with bone interposed between the jaws.

The clamp 52 is shown with the marker and stem 59 removed (by disconnecting the releasable coupling 54 and 56). One member 54 of the releasable coupling can be seen at the top of the bracket; the complementary member 56 is associated with the stem 59 and marker 50 and thus is not visible in this figure.

The releasable coupling facilitates surgery as follows. During surgery, as described above, the femoral tracking marker 50 is initially clamped to a patient's femur via bone clamp 52, with a trackable target 58 initially coupled to the clamp 52 by the releasable coupling (54 and 56). A locating system tracks the femoral tracking marker 50 during an initial geometry acquisition. The locating system also tracks the patient's pelvis and relates the pelvis to the femoral tracking marker. Thus, an initial relationship between the femoral tracking marker and the pelvis is captured and recorded or stored, corresponding to an initial offset and leg length.

Once an initial geometry has been captured, the releasable coupling feature (54 and 56) allows a physician to remove the target 58 and stem 59 from the femoral tracking device, to gain more convenient surgical access to the hip and femur. The bone clamp portion 52 of the femoral tracking marker remains securely fastened to the femur. The optical target can subsequently be reattached to the bone clamp 52 via the coupling 54 and 56, and the previous relationship between the target and the bone will be accurately and reliably reestablished. Reliable tracking of the femur can then resume (for example during surgical navigation steps in a hip replacement surgery.

Figure 4:
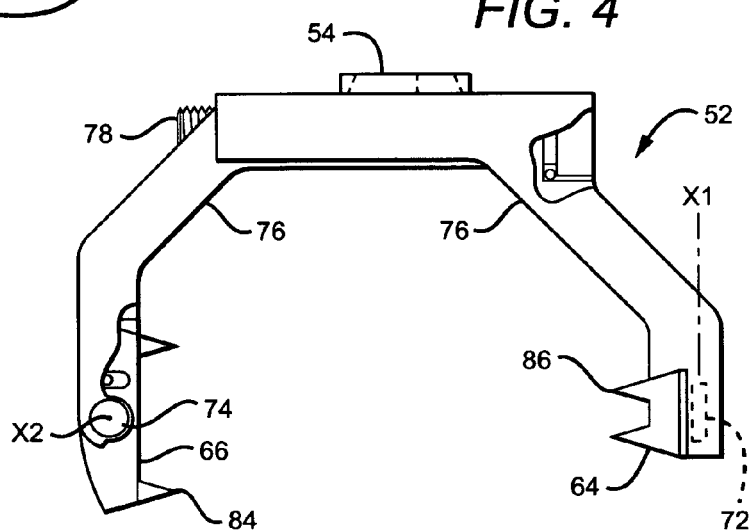
FIG. 4 is a front view of the bone clamp portion of the trackable femoral marker, with trackable target removed and releasable coupling separated.

As shown in FIG. 4 (and in previous FIG. 2), the bone clamp includes two opposable, pivotable jaws: a first jaw 64 pivotable about a first axis X1 (constrained by pivot pin 72) and a second jaw 66 pivotable about a second axis X2 (constrained pivot PIN 74). The first and second axes are preferably constrained to be substantially non-parallel, and in fact the axes X1 and X2 are most preferably constrained to be substantially perpendicular to one another. The two jaws are pivotably connected to a slidable, adjustable bracket 76, the extent of which is preferably adjustable by some mechanism such as a tightening screw 78. The clamp can be attached to a bone by positioning the jaws 64 and 66, then tightening the bracket 76 by shortening its span with the adjustment mechanism 78, thereby urging the opposed first and second jaws toward each other to firmly clamp or pincer the bone as it is compressed between said jaws.

The adjustment mechanism 78 is shown as a screw in FIG. 4. One of the complementary members (54) of a releasable coupling (54 and 56) is also visible on top of the bracket 76, for mating the bracket with a trackable target.

The inventors have found that the arrangement of the jaws with two, substantially perpendicular pivot axes greatly facilitates secure clamping to an irregular bony surface such as that of the greater trochanter. Secure purchase on the bone is also facilitated by gripping features on the jaws. Preferably, each jaw has at least one (most preferably two or more) gripping features such as teeth, fangs, cleats or a sharpened surface texture which tends to firmly engage with a bone surface when pressure is applied between the jaw and the bone surface. However, it is greatly preferred that the gripping features be limited in length to prevent the features from compromising the structural integrity of the cortical shell of the femur. Specifically, the gripping feature should not intrude into the femoral canal, and preferably should not fully penetrate the outer cortical shell of the femur. Two such gripping features (or "teeth") 84 and 86 are shown in the figure by way of example.

The releasable coupling which couples the fixing device to an optically trackable marker has two complementary members: bracket member 54 and complementary member 56.

Figure 5:
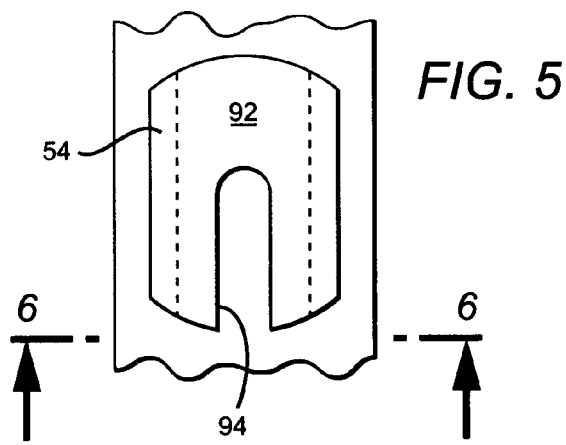
FIG. 5 is a top view of a dovetailed first member of the releasable coupling, useful for removably attaching the bone clamp to the trackable target.
Figure 6:
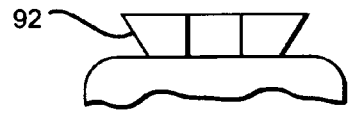
FIG. 6 is a side view of the dovetailed first member shown in FIG. 5.

FIG. 5 shows the bracket member 54 of the releasable coupling (54 and 56 collectively). This coupling reliably establishes a repeatable relationship between trackable target 58 and the bone clamp 52. A dovetailed tongue 92 extends above the top of the bracket 76. The dovetail shape can be seen in FIG. 6 (the end view). Top view of the dovetail shows that it is suitably formed within a partial cylinder, so that the coupling member 54 when assembled with complementary member 56 will together present a cylindrical form. A guide slot 94 is preferably provided to help center and guide the coupling by engaging a center pin 96 carried in the complementary member 56 of the coupling (discussed below).

Figure 7:
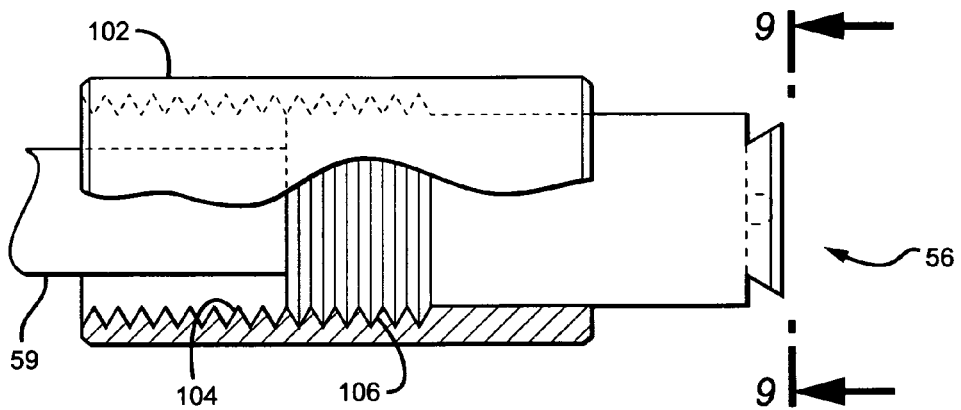
FIG. 7 is a top view of a second member of the releasable coupling, capable of mating with the first member shown in FIGS. 5 and 6.
Figure 9:
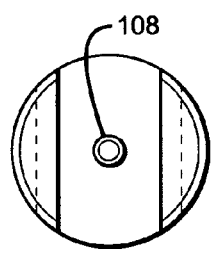
FIG. 9 is a side (end) view of the second member shown in FIGS. 7 and 8.
Figure 8:
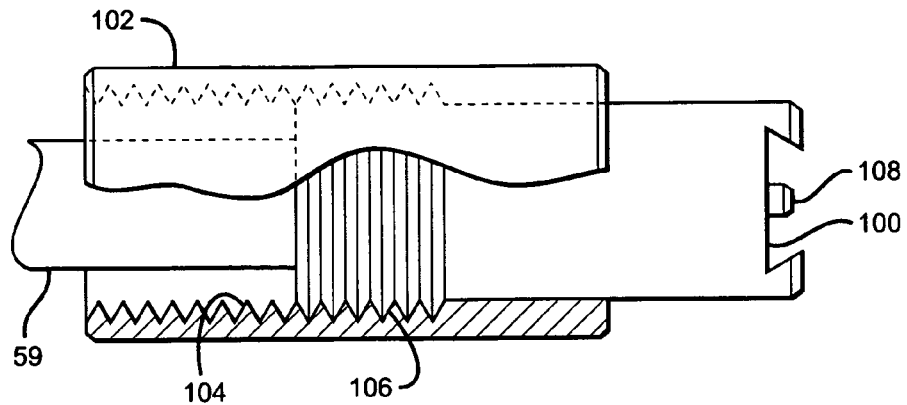
FIG. 8 is a front view of the second member shown in FIG. 7.

As shown in FIGS. 7, 8 and 9, a complementary (or "stem") coupling member 56 is fixed on the optically trackable marker. The stem member 56 has a dovetail slot or void 100 which snugly receives and mates with the dovetail tongue 94 in the bracket member of the coupling. The dovetail slot 100 is preferably cut from a rotationally symmetrical piece (suitably of rigid material such as steel). Preferably, the slot is cut in a cylindrical piece; alternatively, the members 54 and 56 could both be cut from a conical volume. Generalized, the coupling members 54 and 56 should preferably, when fitted together, describe a substantially solid joint which has rotational symmetry. Thus, when mated with the bracket member 54 the dovetailed tongue 92 occupies the dovetail slot 100 so that the two complementary members together comprise a substantially solid volume with rotational symmetry (for example, a cylindrical or a conical volume). Once the coupling members are mated, the mating relationship is fixed and centered by lowering a sleeve 102 to coaxially surround and center the two mated, dovetailed members. (For clarity, the sleeve 102 is shown retracted and disengaged. It should be understood that the sleeve is slidable toward the right in the figure.) The sleeve 102 should preferably have rotational symmetry which corresponds to the exterior shape of the dovetailed joint. For example, a cylindrical sleeve 102 should have an interior dimension which slidably fits and coaxially surrounds the two mated dovetailed members, causing them to tend toward a centered position. The upper portion 104 of the sleeve 102 is suitably threaded with inside threads 104 which engage with complementary threads 106 on an extension post). Rotating the sleeve causes the sleeve to slide over the dovetailed coupling members 54 and 56. The inside cylindrical diameter of the sleeve fits the outside of the cylindrical volume comprising members 54 and 56 and secures the fit of 54 and 56 by containing the cylindrical volume, thereby securing the coupling in a locked and centered position.

Providing rotational symmetry for the dovetailed joint and sleeve is advantageous in that it allows for ease of assembly, yet as the joint is tightened it tends to center the assembly. The coupling is thus self-centering. This produces a reliable, well centered, repeatable fit with little "slop" or error.

A center pin 108 can suitably be provided in the dovetailed slot 100 as shown in FIGS. 7, 8 and 9. This pin engages with a complementary slot 94 in the dovetailed tongue member 92 (previously described and shown in FIG. 5). The center pin 108 and slot 94 facilitate rapid assembly of the coupling by helping to align the dovetailed tongue 92 with the complementary dovetailed slot 100.

Optionally, an elongated stem 59 may used as shown to displace the optical components of the trackable target 58 from the coupling (54 and 56).

The fixing device according to the invention could alternatively be described as a trackable target, capable of fixation to a bone, including: an adjustable bracket having first and second ends and an adjustment mechanism connected to adjust the displacement between the first and second ends; at least two jaws, one connected to each end of the adjustable bracket; a releasable coupling integrated with the bracket; and a trackable member having a compatible coupling which is capable of mating with said releasable coupling in a predictable and repeatable position and orientation. The optically trackable member may optionally be displaced from the coupling and clamp by a substantially rigid stem or other member, which need not be linear in form.

A further aspect of the invention is a Calibrated Patient Positioner which is optionally an integrated component of the navigation system. By way of background, it should be understood that hip replacement surgery may be performed with the patient supine (on his or her back) or in the lateral decubitus position (on his or her side). When the patient is in the lateral position, certain pelvic landmarks may be obscured by soft-tissue, draping, or conventional patient holders. Specifically, these landmarks are known as the pubic symphysis and the (right and left) Anterior Superior Iliac Spines (ASIS). Lack of access to these landmarks makes it difficult for the physician to palpate the pelvic landmarks during the acquisition of initial pelvic geometry.

The present invention provides an alternative to direct palpation to locate the pelvic landmarks. In accordance with the invention, the patient is initially clamped into a calibrated patient positioner which has specific features to "locate" the pelvic landmarks. Instead of palpating the pelvic landmarks directly, a calibrated trackable probe is used to touch distinct points on the positioner itself; given the positions of these distinct points, software extrapolates the positions of the pelvic landmarks. In this way, the calibrated probe need not touch the patient at all; only the positioner must be in contact with the patient.

Figure 11:
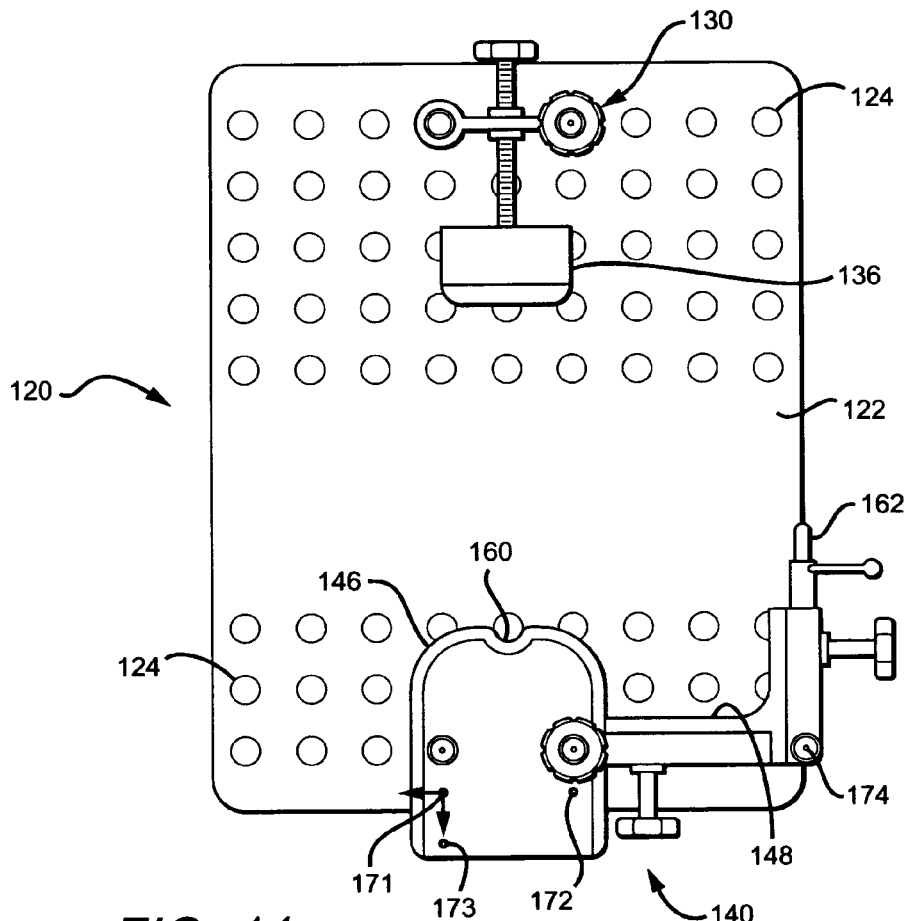
FIG. 11 is a top view of the calibrated patient positioner of FIG. 10.
Figure 10:
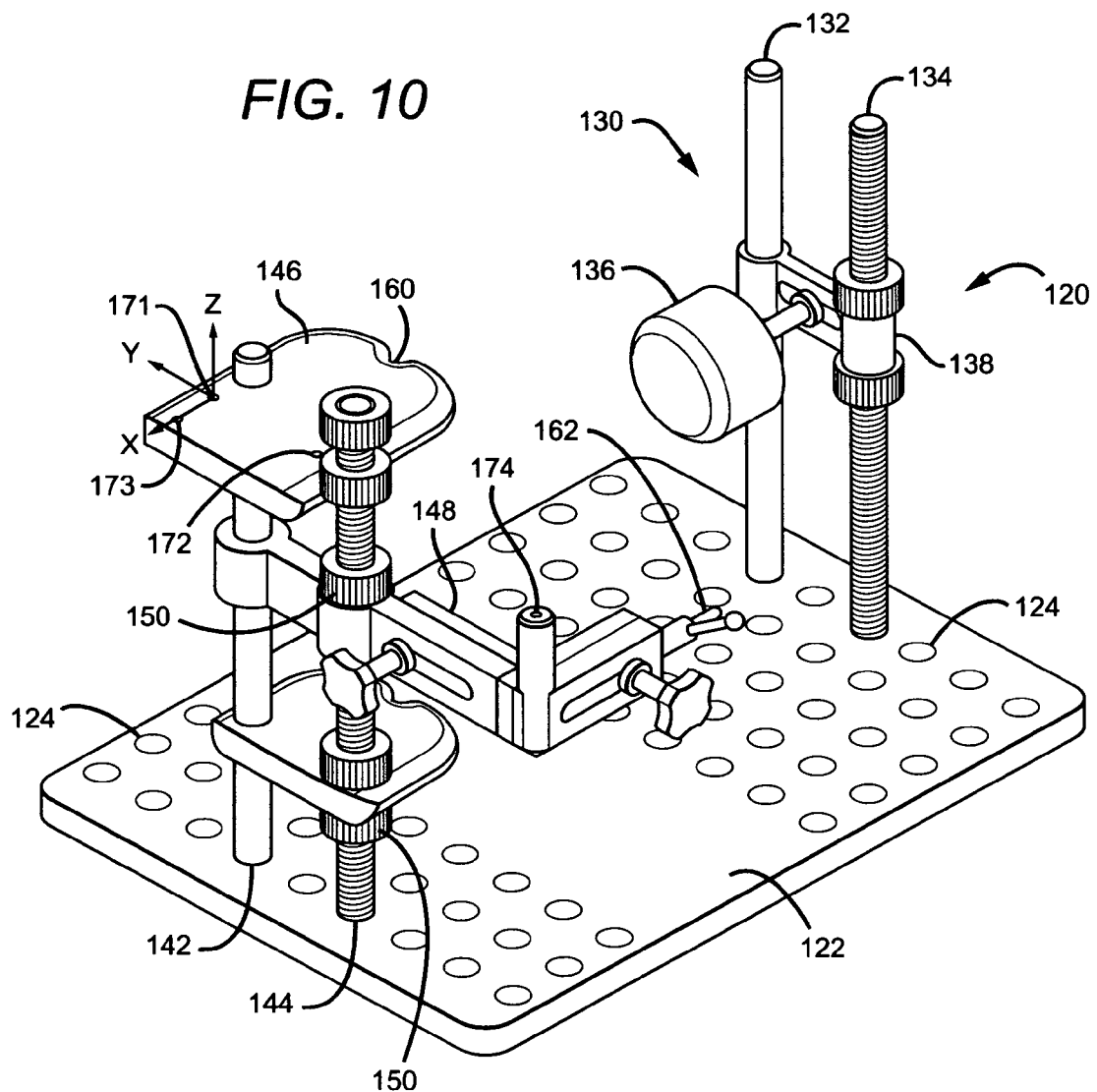
FIG. 10 is an isometric view of a calibrated patient positioner, useful for locating a patient's pelvic plane in accordance with the invention.

FIGS. 10 and 11 show one embodiment of the positioner generally at 120. The device consists of a flat plate 122 preferably perforated with an array of holes 124. Two clamps (not shown) are used to secure the plate 122 to the operating room table. A Back Support Assembly 130 is disposed to support the patient from behind. The back support assembly includes two tower rods 132 and 134, a cushion 136, and a height adjustment and locking mechanism 138. In front of the patient is attached the Front Support Assembly 140, which consists of two tower rods 142 and 144, two ASIS cushions 146, a pubic slide body 148, and a height adjustment and locking mechanism 150.

During set-up for surgery, the patient would be positioned on the operating room table on their side on top of the plate 122. The Back Support Assembly 130 would be inserted into the plate and the patient would be held against the back cushion. The Front Support Assembly 140 would then be inserted and adjusted until the two ASIS's were captured in the two ASIS indicator concavities 160. The pubic slide body 148 and retractable pubic indicator 162 would be then adjusted until the pubic indicator, once extended and locked into place, palpates the pubic symphysis of the patient.

The patient would then be draped and prepared for surgery. The hip joint would be exposed in normal fashion and a pelvic tracker would be attached with a bone screw. After the navigation system is launched, the computer system (32 in FIG. 1) will prompt for palpation of the Calibrated Patient Holder. Using a trackable probe, index points such as 171, 172 and 173 are palpated on the top ASIS cushion assembly 146. Whatever points chosen should have a previously known spatial relationship to the ASIS indicator concavities 160. These index points are then used to define the body coordinate system (x, y, z). Because the top ASIS indicator notch is a fixed, previously known distance from the origin of this coordinate system, the location of the ipsilateral ASIS can be calculated. Point 174 is then palpated and used to calculate the location of the pubic symphysis, based upon a known (or directly measurable) spatial relationship between point 174 and the pubic indicator pointer 162. Because the system assumes symmetry of the pelvis about the Y axis, the contralateral ASIS can be readily calculated. Once the location of both ASIS's and the pubic symphysis are known, the Anterior Pelvic Plane is defined and surgical navigation is enabled. At this point in the procedure, and before releasing the patient from the patient positioner, the locating system and computer will locate the pelvic tracking marker and calculate the relationship between the pelvic marker's orientation and the pelvic plane (as defined with the aid of the patient positioner).

After palpation of point 174 and acquisition of the pelvic marker's orientation, the handle on the pubic indicator can be retracted to remove pressure from the pubic symphysis area. Indeed, after attaching a pelvic tracking marker and acquiring initial geometry, the patient can be released from the frame for repositioning during surgery. The pelvic trackable marker and optical tracker will allow the computer to track the position of the pelvic plane, notwithstanding movement of the pelvis during surgery.

Software should be designed with appropriate provision for input or storage of the spatial relationships between the pelvic landmarks and the indexing points or features (points 171-174) on the positioner. The pelvic landmarks will be constrained or located directly by the indicator concavities and the pubic indicator pointer. The relationships between these pubic landmarks and the index points should be made available to software either by some form of input or by rigidly pre-determining the spatial relationships to dimensions stored as constants. For example, the relationships between the index points and the pelvic landmarks can be fixed by a rigid framework with known dimensions. The known dimensions can then be assumed as constants in computational algorithms.

Figure 12:
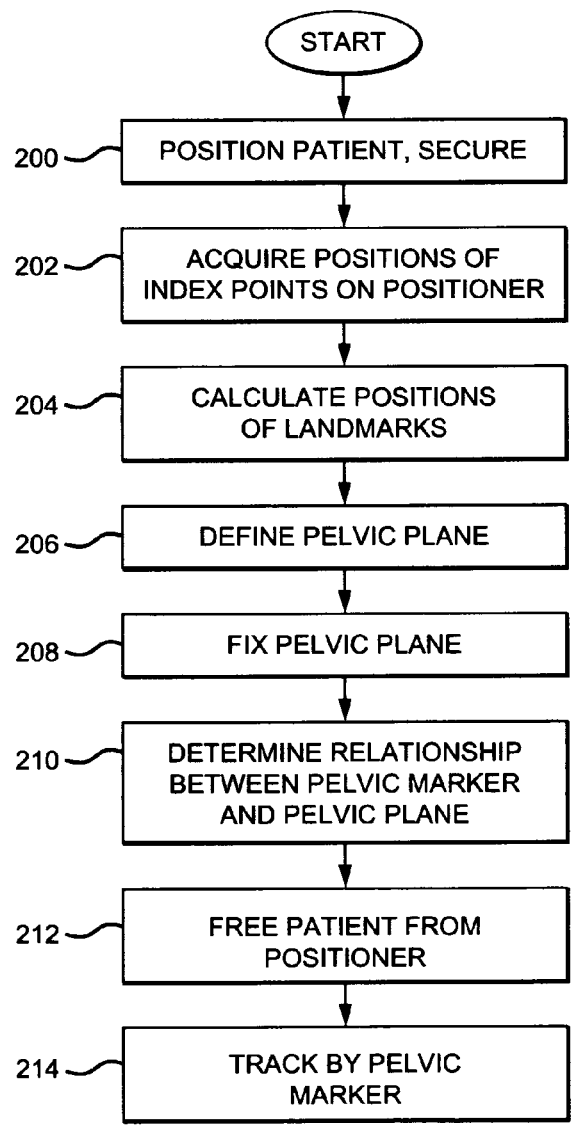
FIG. 12 is a flow diagram of a method for determining a patient's pelvic position and inputting that position into a computer via an optical tracker.

The patient positioner is useful in a method of determining a patient's pelvic position and inputting that position into a computer via an optical (or similar) tracker. Steps of such a method are shown in FIG. 12. The patient is first aligned or positioned in the patient positioner (step 200) as described above, securing the ASIS cusions, ASIS indicator concavities and pubic indicator in contact, with the corresponding pelvic landmarks. The index points 171-174 are then acquired (step 202) suitably by an optical tracker, either by touching the points with a trackable probe or by tracking features mounted directly on the patient positioner at known positions. The computer 32 then calculates (step 204) the positions of the pelvic landmarks by compensating for (known) displacements between the pelvic landmarks and the optically captured index points 171-174. Based on the pelvic landmarks, a reference pelvic plane is then defined (step 206).

In some embodiments, the positions of the index points are captured indirectly by touching the index points individually with a trackable probe. Accordingly, the step of acquiring the positions of a plurality of index points will include, in such embodiments, several steps: touching the index points with the probe; calculating the positions of the trackable probe while the probe is touching the index points; and finally, compensating for a known dimension and shape (geometry) of the trackable probe.

After calculating the pelvic plane, an optically trackable pelvic marker is then fixed to the patient's pelvis (step 208, for example, by a bone screw). The computer then determines and stores the spatial relationship between the trackable pelvic marker and the pelvic plane (step 210). This can be done suitably by determining a reference frame defined by the pelvic tracking marker (for example, of reflective optical targets) and comparing it to the pelvic plane (while the patient is still positioned in the patient positioner). From the two frames a computer calculates a coordinate transformation between the marker reference frame and the pelvic plane (and/or the inverse transformation).

After determining the relationship between the pelvic tracking marker and the pelvic plane, the patient's pelvis can be freed from the positioner (step 212). The pelvic plane is then indirectly tracked (step 214) by tracking the pelvic tracking marker (which is fixed to the pelvis). The corresponding orientation of the pelvic plane is easily obtained by applying (to the tracker orientation) the previously calculated coordinate transformation, to obtain the pelvic plane. With an appropriate optical tracker as described above, coupled with modest computing speed, the pelvic plane can easily be dynamically tracked in real time without significant time lag.

The Calibrated patient positioner and the method of using it to acquire and track a pelvic plane can advantageously be employed in connection with the computer assisted surgical methods as described elsewhere.

While several illustrative embodiments of the invention have been shown and described, numerous variations and alternate embodiments will occur to those skilled in the art. In some operations the acetabular implant might not be required, but the femoral navigation methods and apparatus of the invention are still applicable. The procedure may be repeated on both sides of the body in a bi-lateral THR operation. Different elastomeric straps, fibers, cords, mesh, wire, adhesives or ligatures could be employed in connection with the femoral tracking marker device. The fixed pelvic marker could also be fixed by alternate methods such as clamps, pins or even adhesives. The method can be adapted to various body geometries and sizes, and indeed could even be adapted, with small modifications, for veterinary medicine. Tracking means other than but similar to optical could be substituted, such as radio, microwave, magnetic, sonic or ultrasonic tracking systems, provided that the system be not so clumsy or bulky as to interfere with the surgical manipulations required. Accordingly, the word "tracking" as used herein should be understood to include methods other than optical, but is not intended so broadly as to encompass mere mechanical stereotactic frameworks or electromechanical stereotactic frameworks. The geometries of the various tools and markers can be varied or modified to accommodate different tracking approaches. Active or passive optical targets can be used on the tracking markers. Such variations and alternate embodiments are contemplated, and can be made without departing from the spirit and scope of the invention as defined in the appended claims.

We claim:

1. A method of determining a surgical patient's pelvic position and inputting that position into a computer via a tracking system, suitable for use in navigating partial or total hip replacement surgery, comprising the steps of:
   aligning the patient in relation to a patient positioning frame with pelvic anatomical features of the patient disposed in secure mechanical relationship with corresponding locating features on said positioning frame;
   acquiring with a tracking system the positions of a plurality of index points, wherein each of said index points is respectively disposed at a previously known displacement relative to a corresponding one of said locating features; and
   defining a pelvic plane by calculation from the acquired positions of said index points, said calculation including:
      compensating for the previously known displacement of each said index point relative to its corresponding locating feature, thereby finding the locations of said locating features from the acquired positions of said index points; and
      defining a plane from the calculated positions of the locating features, such that said pelvic plane is defined based on the locations of said pelvic anatomical features disposed in said secure mechanical relationship with said corresponding locating features.

2. The method of claim 1, wherein said pelvic anatomical features are the right Anterior Superior Iliac Spine (ASIS), the left ASIS, and the pubic symphysis;
   and wherein said locating features comprise three locating features arranged to engage said right ASIS, left ASIS, and pubic symphysis respectively, such that said three locating features define the pelvic plane.

3. A method of determining a surgical patient's pelvic position and inputting that position into a computer via a tracking system, suitable for use in navigating partial or total hip replacement surgery, comprising the steps of:
   aligning the patient in relation to a patient positioning frame with pelvic anatomical features of the patient disposed in secure mechanical relationship with corresponding locating features on said positioning frame;
   acquiring with a tracking system the positions of a plurality of index points, wherein each of said index points is respectively disposed at a previously known displacement relative to a corresponding one of said locating features; and
   defining a pelvic plane by calculation from the acquired positions of said index points, said calculation including:
      compensating for the previously known displacement of each said index point relative to its corresponding locating feature, thereby finding the locations of said locating features from the acquired positions of said index points; and
      defining a plane from the calculated positions of the locating features,
   wherein said pelvic anatomical features are the right Anterior Superior Iliac Spine (ASIS), the left ASIS, and the pubic symphysis;
   wherein said locating features comprise three locating features arranged to engage said right ASIS, left ASIS, and pubic symphysis respectively, such that said three locating features define the pelvic plane; and
   wherein said locating features include a retractable pubic indicator which is adjustable to palpate the patient's pubic symphysis.

4. The method of claim 3, wherein said locating features further include at least one ASIS indicator concavity carried by a front support assembly of said patient positioning frame.

5. The method of claim 4, wherein said patient positioning frame further comprises a rear support assembly arranged adjustably to include the patient securely between said front support assembly and said rear support assembly.

6. The method of claim 3, wherein said step of acquiring with a tracking system the positions of a plurality of index points comprises:
   touching said index points with an optically trackable probe;
   calculating the position of said optically trackable probe while said probe is touching said index points; and
   compensating for a known dimension and shape of said probe.

7. The method of claim 1, comprising the further steps:
   fixing a trackable pelvic marker to the patient's pelvis;

tracking the position and orientation of said trackable pelvic marker while said pelvic plane is fixed in relation to said patient positioning frame;

calculating a spatial relationship between the trackable pelvic marker and the defined pelvic plane;

releasing the patient's pelvis from said patient positioning frame; and tracking the pelvic plane indirectly by tracking the position and orientation of said trackable pelvic marker then applying a coordinate transformation to calculate the pelvic plane, from time to time.

8. The method of claim 7, wherein said trackable pelvic marker is fixed to the patient's pelvis by a bone screw.

9. The method of claim 8, wherein said trackable pelvic marker comprises a marker with either reflective or active trackable optical targets.

* * * * *